United States Patent [19]

Kiefer et al.

[11] 4,038,311
[45] July 26, 1977

[54] PRODUCTION OF N-(1-ALKENYL)-CARBAMYL CHLORIDES

[75] Inventors: Hans Kiefer, Wachenheim; Herbert Naarmann, Wattenheim, both of Germany

[73] Assignee: BASF Aktiengesellschaft, Ludwigshafen (Rhine), Germany

[21] Appl. No.: 533,143

[22] Filed: Dec. 16, 1974

Related U.S. Application Data

[63] Continuation-in-part of Ser. No. 887,346, Dec. 22, 1969, abandoned.

[30] Foreign Application Priority Data

Jan. 14, 1969 Germany .............................. 1901542

[51] Int. Cl.$^2$ ............................................ C07C 125/03
[52] U.S. Cl. .................................. 260/544 C; 71/98; 106/2; 162/168 N; 260/77.5 CR; 260/453 A; 260/453 RL; 260/455 A; 260/534 R; 260/543 P; 260/553 A; 260/557 R; 260/874; 260/938
[58] Field of Search .................................... 260/544 C

[56] References Cited

U.S. PATENT DOCUMENTS

| | | | |
|---|---|---|---|
| 3,501,523 | 3/1970 | Sayigh | 260/544 C |
| 3,824,280 | 7/1974 | Kiefer et al. | 260/544 C |
| 4,001,318 | 1/1977 | Botta | 260/544 C |

FOREIGN PATENT DOCUMENTS

| | | |
|---|---|---|
| 744,409 | 7/1970 | Belgium |
| 763,948 | 7/1967 | Canada |
| 980,262 | 1/1965 | United Kingdom |

OTHER PUBLICATIONS

Breederveld. Rec. Trav. Chim. Pays–Bas 79, 1197–1202 (1960).

*Primary Examiner*—Ethel G. Love
*Attorney, Agent, or Firm*—Johnston, Keil, Thompson & Shurtleff

[57] ABSTRACT

The production of N-(1-alkenyl)-carbamyl chlorides by reaction of a Schiff base with phosgene, and the new N-(1-alkenyl)-carbamyl chlorides themselves. The new compounds which can be prepared by the process of the invention are valuable starting materials for the production of coating intermediates, plastics, paints and plant protection agents.

One preferred group of compounds available from said process are the N-vinyl compounds of the formula

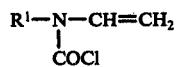

in which $R^1$ is cyclohexyl, cyclooctyl, norbornyl, tetrahydrodicyclopentadienyl, n-hexyl, n-octyl, 2-ethylhexyl or phenyl. Another preferred group of compounds are the N-vinyl-N-t-alkylcarbamyl chlorides of 4 to 6 carbon atoms in the tertiary alkyl group, especially N-vinyl-N-t-butylcarbamyl chloride.

7 Claims, No Drawings

PRODUCTION OF N-(1-ALKENYL)-CARBAMYL CHLORIDES

This application is a continuation-in-part of our Application Ser. No. 887,346 filed on Dec. 22, 1969, now abandoned.

The invention relates to a process for the production of N-(1-alkenyl)-carbamyl chlorides by reaction of a Schiff base with phosgene and new substances of this type.

It is known from Rec. Trav. Chim. Pays-Bas, 79, 1197 et seq. (1960), that it is possible to add on organic acid chlorides to N-propylpropanaldimes to form the corresponding N-(1-chloropropyl)-N-propyl acid amides. These adducts lose hydrogen chloride when heated with triethylamine and are converted into the corresponding N-(1-propenyl)-N-propyl acid amides. Reference is made there to the fact that acid chlorides which react with triethylamine (for example acetyl chloride) have first to be reacted with the Schiff base and the base is added only after this reaction (addition) has taken place. Reaction of silicon tetrachloride or sulfuryl chloride instead of the organic acid chlorides does not proceed in the said manner and yields different end products.

One object of the invention is a new process for the production of N-(1-alkenyl)-carbamyl chlorides in good yields and high purity.

Another object of this invention is the new N-(1-alkenyl)-carbamyl chlorides.

These and other objects of the invention are achieved and N-(1-alkenyl)-carbamyl chlorides having the formula

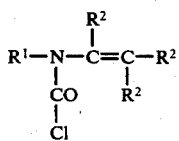

(I), wherein $R^1$ and $R^2$ each denotes an aliphatic, cycloaliphatic, araliphatic or aromatic radical, each individual radical $R^2$ may also denote hydrogen and any two radicals $R^2$ may further be combined to form at least one carbocyclic ring of 5 to 7 members, are obtained advantageously by reacting phosgene at a temprature of $-30°$ to $+150°$ C with a Schiff base having the formula

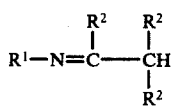

(II), where $R^1$ and $R^2$ have the same meanings given above and are essentially inert under the reaction conditions and in the presence of an additional base selected from the class consisting of tertiary amines and alkali metal carbonates.

When acetaldehyde isopropylimine is used, the reaction may be represented by the following equation:

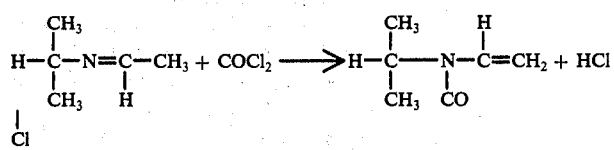

When compared with the state of the art, the process according to this invention provides, surprisingly, a large number of N-(1-alkenyl)-carbamyl chlorides in a simple way, in good yield and in high purity. Phosgene may be reacted with the Schiff base, if desired in the presence of triethylamine, in a single stage. In Rec. Trav., examples of inorganic acid chlorides which are reacted with N-propyl-N-propenylaldimine are $(C_2H_5)_2NSiCl_3$, $POCl_3$, $SiCl_4$ and $SO_2Cl_2$, of which $SiCl_4$ and $SO_2Cl_2$ react in a different way with the Schiff base; one could not therefore have expected that this reaction could be extended to cover inorganic acid chlorides generally, e.g., the reaction of Schiff bases with phosgene. Breederveld expressly mentions heating (p. 1197, last paragraph) of the saturated addition compound I, or recommends addition of the aldimine to a boiling solution of acid chloride + amine (bottom of page 1198). In contrast to this the end products I can be produced simply and without amine with phosgene and at fairly low temperatures.

Moreover, the fact that the N-1-alkenyl-n-alkylcarbamoyl chlorides do not react with excess Schiff base to form ureas suggests that Breederveld's reaction is not generally applicable. Nor can the reaction of $POCl_3$ or $(C_2H_5)_2 NSiCl_3$ with a Schiff base be extended to inorganic acid chlorides generally. Unlike the reaction of a Schiff base with phosgene, the reaction of imines with $POCl_3$ does not proceed uniformly. Thus the intermediate

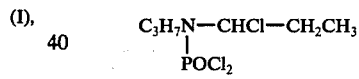

reacts extensively with N-propylpropanaldimine to form

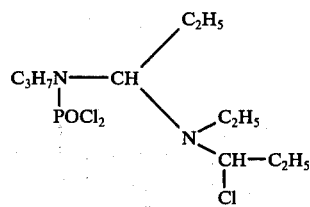

Schiff bases of aldehydes or ketones with primary amines having the formula (II) are used as starting materials. Preferred starting materials (II) and consequently preferred end products (I) are those in whose formulae the individual radicals $R^1$ and $R^2$ may be identical or different and each denotes an alkyl radical, particularly one having from 1 to 20 and preferably from 1 8 carbon atoms, a cycloalkyl radical, particularly one having from 5 to 12 and preferably from 5 to 7 carbon atoms, an aralkyl radical, particularly one having 7 to 12 carbon atoms, or a phenyl radical, and the individual radicals, $R^2$ may also denote hydrogen atoms and/or any two of the radicals $R^2$ may be members of a five-membered to seven-membered carbocyclic ring. In the preferred starting materials (II) all the radicals R² may also be members of a bicyclic compound having a five-membered to seven-membered carbocyclic rings, one radical R² being a member of one ring, a second radical R² being a member of the other ring and the third radial R² being simultaneously a member of both rings. R¹ may also denote a polycycloalkyl radical, particularly a bicycloalkyl radical having 7 to 10 carbon atoms or a tricycloalkyl radical having 7 to 12 carbon atoms. The said radicals may also bear, as substituents, groups and/or atoms which are inert under the reaction conditions, for example chlorine atoms, bromine atoms, trifluoroalkyl groups, alkoxy groups, alkylthio groups and alkysulfonyl groups, each group having 1 to 4 carbon atoms, nitro groups or phenoxy groups.

For example the following Schiff bases may be used as starting materials (II): isopropylimines, cyclohexylimines, n-propylimines, benzylimines, methylimines, ethylimines, n-propylimines, n-butylimines, tert-butylimines, 2-ethylhexylimines, 1-octadecylimines, methylcyclohexylimines, cyclooctylimines, cyclododecylines, norbornylimines, tetrahydrodicyclopentadienylimines, o-toluylimines, m-toluylimines, p-toluylimines, o-chlorophenylimines, 3,4-dichlorophenylimines, m-methylsulfonylphenylimines, p-chlorophenoxyphenylimines, p-fluorophenylimines and phenylimines of propionaldehyde, n-butyraldehyde, isobutyraldehyde, 2-methylvaleraldehyde, 2-ethylcaproic aldehyde, phenylacetaldehyde, diethyl ketone, cyclopentanone, cyclohexanone, cyclooctanone, cyclododecanone, norbornanone, tetrahydrodicyclopentadienone, acetophenone, isophorone, methylisobutyl ketone, acetone, methyl ethyl ketone and preferably of acetaldehyde Paricularly preferred starting materials (II) and end products (I) are those in which R¹ denotes cyclooctyl, cyclohexyl, isopropyl, n-propyl, ethyl, n-butyl, sec-butyl, tert-butyl, norbornyl, 2-ethylhexyl, n-octyl, n-hexyl, tetrahydrodicyclopentadienyl or phenyl, and in which R² denotes hydrogen or in which any two of the radicals R² may be combined to form one carbocyclic ring of 5 to 7 members.

For example, the following Schiff bases may be used as particularly preferred starting materials (II): cyclooctylimines, isopropylimines, cyclohexylimines, n-propylimines, ethylimines, sec-butylimines, n-butylimines, norbornylmines, tert-butylimines, 2-ethylhexylimines, n-octylimines, n-hexylimines, tetrahydrodicyclopentadienylimines, phenylimines of cyclopentanone, cyclohexanone, cycloheptanone, norboranone and preferably of acetaldehyde.

Among these preferred Schiff bases the following are preferably used as starting materials (II): isopropylimines, cyclohexylimines, n-butylimines and particularly tert-butylimines of acetaldehyde.

The starting material (II) may be reacted with phosgene in a stoichiometric amount or in excess, for example in a ratio of 1 to 1.2 moles of phosgene per mole of starting material (II). The reaction is advantageously carried out in the presence of a base, usually in the presence of a tertiary amine, in an amount of from 1 to 1.5 moles per mole of starting material (II). The suitable bases are tertiary amines such as triethylamine or pyridine; alkali metal carbonates such as potassium carbonate or sodium carbonate. The reaction is carried out at a temperature of from −30° to +150° C, preferably from 0° to 110° C, at atmospheric or superatmospheric pressure, continuously or batchwise. Organic solvents which are inert under reaction conditions such as aromatic hydrocarbons, for example benzene or toluene; chlorohydrocarbons, for example carbon tetrachloride, trichlorethylene; ethers, for example diethyl ether or dioxane; alicyclic hydrocarbons, for example cyclohexane; or mixtures of the same, may be used if desired.

The reaction may be carried out as follows: phosgene is passed for one hour to three hours at the reaction temperatures into the starting material (II) which is usually mixed with the base and/or solvent. Phosgene may also be placed in a vessel with a solvent, and the base and starting material (II) with or without solvent may be added to the mixture. Furthermore, a mixture of all the components may be prepared without the base in the manner described and then the base may be added to the mixture to the base. After all the components have been added it is advantageous to stir the mixture for another 30 minutes to 4 hours. The unreacted phosgene is then removed from the mixture, for example by passing a current of nitrogen, and the mixture is filtered. The filter reidue (the hydrochloride of the amine formed during the reaction) is washed with one of the said solvents. The filtrates obtained are united and the end product is isolated therefrom by a conventional method, for example by fractional distillation.

The new compounds which may be prepared by the process according to the invention are valuable starting materials for the production of coating intermediates, plastics, paints and plant protection agents. Thus the N-(1-alkenyl)-ureas described in Belgian Patent Specification No. 702,425 as phytotoxic substances may, for example, be prepared therefrom by reaction with arylamines. Furthermore they may be copolymerized with other monomers, for example acrylates, methacrylates and styrene. With regard to copolymerization, reference is made to Hoube-Weyl, "Methoden der organischen Chemie", 14/1,page 24 (1961). The copolymers may be used as coatings or films on building materials, for example surfaces of wood, stone or concrete, as shown in Examples 6 and 8. Such coatins or films may be manufactured in any desired manner by an known method (Ullmanns Encyklopadie der techischen Chemie, 11, page 283, 367 et seq. (1960). Crosslinking agents for polyamines may also be prepared from the end products (I) by polymerization as shown by Example 7, Crosslinking of polyamines may be carried out by methods described in the said volume of the work by Houben-Weyl. Surface coatings and films based on these polymer products exhibit good film strengths, uniform and relatively rapid drying especially in the case of large areas, adhesion, and good elasticity with sufficient hardness on wood, concrete and stones. Large-area coatings give a pleasant and not too dull a gloss and exhibit satisfactory light fastness. It is the copolymers, too, which form a good film with not brittleness and which are therefore also suitable for multilayer coatings.

The following test and Examples 6 to 8 and 14 to 19 illustrate the utility of the end products (I).

The end product (I) of the formula

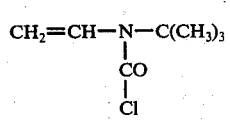

A and its homologs are components belonging to the enamine class. In contrast to enamines such as

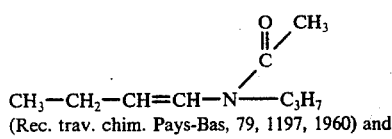
(Rec. trav. chim. Pays-Bas, 79, 1197, 1960) and

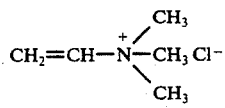

which are not polymerizable by free radical mechanisms, the compound according to the invention may be polymerized as the following comparative example shows. 50 parts of each of compounds A, B and C has added to it 50 parts of toluene and 0.1 part of azobisisobutyronitrile and the whole heated for 10 hours at 75° C. In the case of A a viscous solution is obtained having a dry content of 42% and a polymer having a K value of 49.5. In the case of both B and C no polymer was obtained.

Whereas 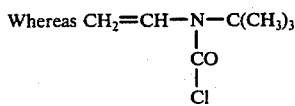 A reacts in equimolar proportions with tert-buty hydroperoxide in the presence of pyridine at 20° C (10% in toluene) to give a peroxide of the formula

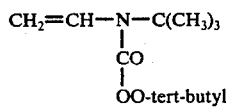 D, the analogous reaction with

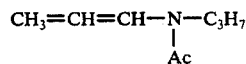 E, (Ac is an acylic radical, e.g. $CH_3$—CO —, Lit, Rec. trav. chim. Pays-Bas, 79 (1960)) is unsuccessful.

D, the derivative prepared from the acid chloride of the invention, also reveals a surprising effect, viz., it undergoes polymerization under the conditions of Example 6. This surprising behavior is explained in the following example: 90 parts of methyl acrylate and 100 parts of toluene are added to 10 parts of

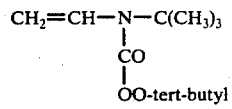 D and the whole heated for 6 hours at 80° C.

A viscous solution is obtained having a dry content of 45.5% by weight. The polymer formed has a K value of 62 and contains free isocyanate groups formed by decomposition of the unsaturated peroxide. This effect is unexpected and cannot be achieved with any of the said prior art products. A copolymer containing

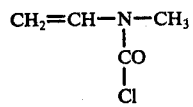

and methyl acrylate which is heated for 1 hour at 100°C in the presence of 1% by weight of boron trifluoride diethyl etherate, 10% in toluene, demonstrates no reaction.

However, under analogous conditions the copolymer with A does react; it forms a gas, identified as tert-butyl chloride, and isocyanate groups are detectable in the copolymer. It was not possible from the state of the art to derive either the special properties given and shown or the utility and surprising behavior of the end products.

Reaction of the carbamyl chlorides I with alcohols give N-vinyl-N-alkyl carbamic esters which, as disclosed in German Pat. No. 1,173,454, are interesting monomers. Specific examples of comounds obtainable from the claimed compounds I are N-vinyl-n-methyl, N-vinyl-N-ethyl, N-vinyl-N-propyl, N-vinyl-N-butyl, N-vinyl-N-isopropyl, N-vinyl-N-sec-butyl and N-vinyl-N-tert-butyl carbamic esters.

N-alkenyl-N-alkylamides of the formula

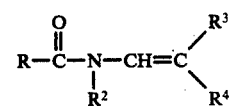

are obtained by reacting carbamyl chlorides I with organometallic compounds RMX, for example

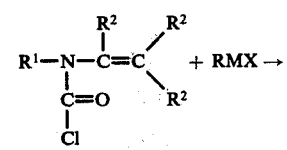

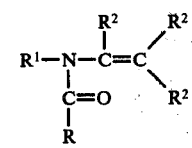

These compounds, too, are valuable monomers. Thiolcarbamates of the formula

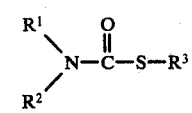

can be used as herbicides. They are prepared by reacting N-alkenylcarbamyl chlorides I with mercaptans, e.g., N-isopropyl-N-(methyl-1-vinyl-1)-carbamyl chloride with 2,3,3-trichloroallyl mercaptan giving the herbicide

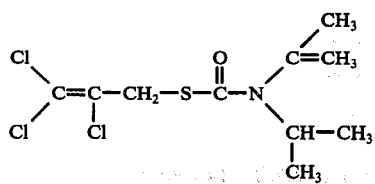

(Details of such thiocarbamates and derivatives show U.S. Pat No. 3,330,821 and U.K. Pat No. 1,010,741.)

The 1-alkenyl isocyanates shown in German Published Application DOS 1,922,412

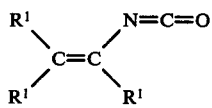

are obtained by thermal cracking, in contact with metal compounds, of N-(1-alkenyl)-N-tert-alkylcarbamyl chlorides I; for example N-tert-buty-N-vinylcarbamyl chloride gives vinyl isocyanate:

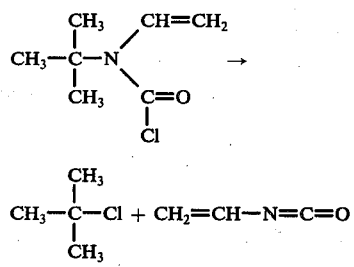

which is a valuable monomer. In particular, N-vinyl-n-tert-pentylcarbamyl chloride and N-vinyl-N-tert-hexylcarbamyl chlorides can be cracked in this way to form the corresponding vinyl isocyanates and tert-alkyl chlorides:

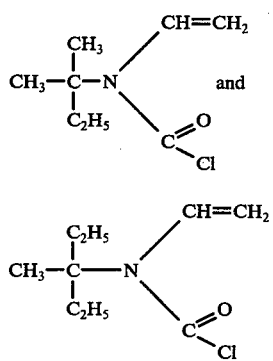

DOS No. 1,925,196 discloses as herbicides ureas of the general formula

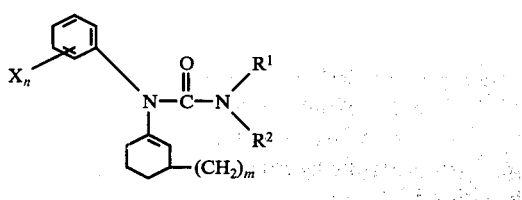

which are prepared by reacting the corresponding N-aryl-N-alkenylcarbamyl chlorides I with amines or anilines, e.g.

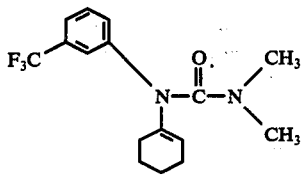

N-phenyl-N-1-cyclohexenyl dimethylurea, N-p-chlorophenyl-N-1-cyclohexenyl-N', N'-dimethylurea, N-p-bromophenyl-N-1-cyclohexenyl-N',N'-dimethylurea, N-3,4-dichlorophenyl-N-1-cyclohexeneyl-N', N'-dimethylurea, N-phenyl-N-1-cyclopentenyl-N', N'-dimethylurea.

Herbicidal urea derivatives suitable for controlling the growth of unwanted plants in soybeans are prepared from ureidophenols and alkenyl carbamyl chlorides I, e.g.

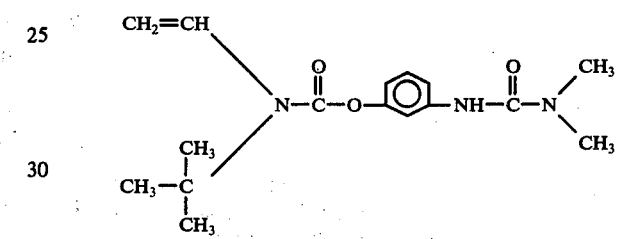

from N-vinyl-N-tert-butylcarbamyl chloride I.

Insecticidal carbamic esters are obtained by reacting phenols with n-alkenyl-N-carbamyl chlorides: from N-vinly-N-methylcarbamyl chloride: e.g.

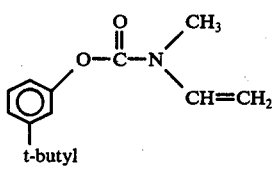

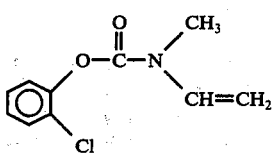

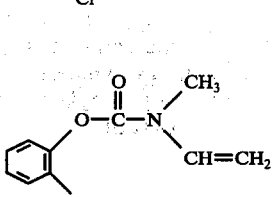

from N-propenyl-N-methylcarbamyl chloride:

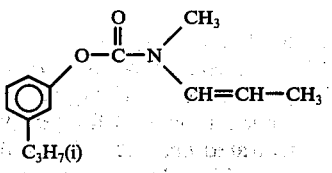

-continued

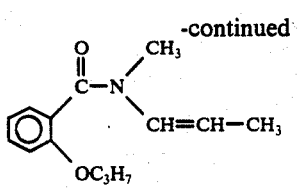

from N-isobutenyl-N-methylcarbamyl chloride:

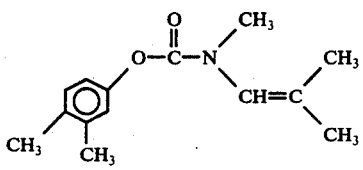

oil repellents are prepared by reacting a N-1-alkenyl-N-alkylcarbamyl chloride I with a fluorinated amine in the presence of an acid-binding substance, for example

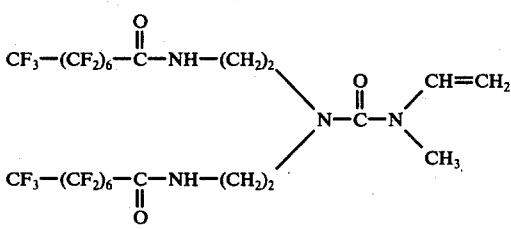

and

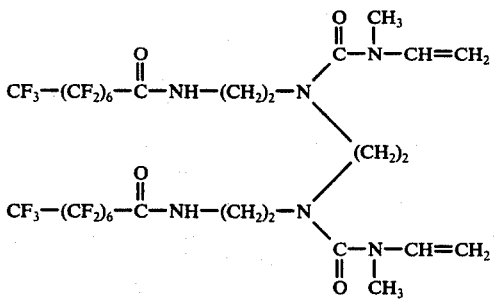

from N-vinyl-N-methylcarbamyl chloride and the appropriate amino compounds.

The following are given in particular as end products:
N-vinyl-N-methylcarbamyl chloride, p N-vinyl-N-ethylcarbamyl chloride, N-vinyl-N-n-propylcarbamyl chloride, N-vinyl-N-isopropylcarbamyl chloride, N-vinyl-N-n-1-butylcarbamyl chloride, N-vinyl-N-n-2-butylcarbamyl chloride, N-vinyl-N-tert-butylcarbamyl chloride, N-vinyl-N-cyclohexylcarbamyl chloride, N-vinyl-N-cyclooctylcarbamyl chloride, N-vinyl-N-norbornylcarbamyl chloride, N-vinyl-N-tetrahydrodicyclopentadienylcarbamyl chloride, N-1-propenyl-N-methylcarbamyl chloride, N-2-propenyl-N-methylcarbamyl chloride, N-1-butenyl-N-methylcarbamyl cloride, N-1-methyl-1propenyl-N-methylcarbamyl chloride, N-2-methyl-1-propenyl-N-methylcarbamyl chloride, N-1-ethyl-1-hexenyl-N-methylcarbamyl chloride, N-1-cyclohexenyl-N-methylcarbamyl chloride, N-1cyclooctenyl-N-methylcarbamyl chloride, N-1-cyclopentenyl-N-methylcarbamyl chloride, N-isopropyl-N-2-phenylvinylcarbamyl chloride, N-1-cyclohexenyl-N-phenylcarbamyl chloride, N-1-cyclopentenyl-N-phenylcarbamyl chloride, N-1-cyclohexenyl-N-o-methylphenylcarbamyl chloride, N-1-cyclohexenyl-N-o-chlorophenylcarbamyl chloride, N-1-cyclohexenyl-N-chlorophenylcarbamyl chloride, N-1-cyclohexenyl-N-3,4-dichlorophenylcarbamyl cloride, N-1cyclohexenyl-N-m-methylsulfonylphenylcarbamyl chloride, N-1-cyclopentenyl-N-p-chlorophenoxyphenylcarbamyl chloride, N-1-cyclohexenyl-N-m-trifluoromethylphenylcarbamyl chloride, N-1-cyclohexenyl-N-p-bromophenylcarbamyl chloride and N-cyclopentenyl-N-p-fluorophenylcarbamyl chloride.

End products which are preferred for the said uses are: N-(1-alkenyl)-carbamyl chlorides having the formula

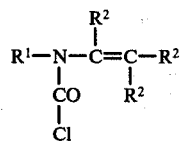

(I)

in which $R^1$ denotes cyclooctyl, cyclohexyl, isopropyl, n-propyl, ethyl, n-butyl, sec-butyl, tert-butyl, norbornyl, 2-ethylhexyl, n-octyl, n-hexyl, tetrahyrodicyclopentadienyl or phenyl, and in which $R^2$ denotes hydrogen or in which any two of the radicals $R^2$ denotes hydrogen or in which any two of the radicals $R^2$ may be combined to form one carbocyclic ring of 5 to 7 members.

The following are given as preferred end products:
N-vinyl-N-methylcarbamyl chloride,
N-vinyl-N-ethylcarbamyl chloride,
N-vinyl-N-n-propylcarbamyl chloride,
N-vinyl-N-isopropylcarbamyl chloride,
N-vinyl-N-n-1-butylcarbamyl chloride,
N-vinyl-N-sec-butylcarbamyl chloride,
N-vinyl-N-tert-butylcarbamyl chloride,
N-vinyl-N-cyclohexylcarbamyl chloride,
N-vinyl-N-cycloocytylcarbamyl chloride,
N-vinyl-N-norbornylcarbamyl chloride,
N-vinyl-N-tetrahydrodicyclopentadienylcarbamyl chloride,
N-vinyl-N-octylcarbamyl chloride,
N-vinyl-N-2-ethylhexylcarbamyl chloride,
N-vinyl-N-hexylcarbamyl chloride,
N-vinyl-N-phenylcarbamyl chloride.

Particularly preferred end products are N-cyclohexyl-, N-isoropyl, N-n-butyl- and especially N-tert-butyl-N-vinylcarbamyl chloride.

The examples, in which the parts given are by weight, illustrate the invention.

EXAMPLE 1

N-vinyl-N-isopropylcarbamyl chloride:

110 parts of phosgene is passed in the course of two hours at 35° to 40° C into a solutoion of 85 parts of acetaldehyde isopropylimine and 113 parts of triethylamine in 300 parts of benzene. Unreacted phosgene is then expelled by means of a stream of nitrogen and the triethylamine hydrochloride formed is filtered off. The filter residue is washed with a little benzene and the solvent is distilled off from the combined filtrates. The distillation residue is fractionally distilled in vacuo. 125 parts (85% of the theory) of N-vinyl-N-isopropylcarbamyl chloride is obtained having a boiling point of 65° C at 2 mm. The structure of the end product is confirmed by analysis and by infra-red and nuclear magnetic resonance spectra.

EXAMPLE 2

N-vinyl-N-cyclohexylcarbamyl chloride:

In a manner analogous to Example 1, the reaction is carried out with 125 parts of acetaldehyde cyclohexylimine instead of acetaldehyde isopropylimine. 150 parts (80% of the theory) of N-vinyl-N-cyclohexylcarbamyl chloride is obtained as a colorless oil having a boiling point of 74° C at 0.4 mm.

EXAMPLE 3

N-(1-propenyl)-N-propylcarbamyl chloride:

In a manner analogous to Example 1, the reaction is carried out with 99 parts of propionaldehyde propylimine as the Schiff base, with 87 parts of triethylamine and with 400 parts of carbon tetrachloride as solvent. 140 parts (87% of the theory) of N-(1-propenyl)-N-propylcarbamyl chloride having a boiling point of 69° C at 2.5 mm is obtained.

EXAMPLE 4

N-isopropenyl-N-cyclohexylcarbamyl chloride:

139 parts of acetone cyclohexylimine and 11 parts of triethylamine are dissolved in 500 parts of carbon tetrachloride, and the whole reacted with 100 parts of phosgene as described in Example 1. 123 parts (61% of the theory) of N-isopropenyl-N-cyclohexylcarbamyl chloride is obtained having a boiling point of 85° C at 0.01 mm.

EXAMPLE 5

N-isopropenyl-N-isopropylcarbamyl chloride:

99 parts of acetone isopropylimine and 94 parts of triethylamine are dissolved in 400 parts of methyl chloride, and the whole reacted with 120 parts of phosgene at a temperature of 30° to 40° C, as described in Example 1. After isolation, 131 parts (81% of the theory) of N-isopropenyl-N-isopropylcarbamyl chloride is obtained having a boiling point of 69° C at 3 mm.

EXAMPLE 6 (application)

100 parts of methyl acrylate, 200 parts of toluene and 1 part of azobisisobutyronitrile are added to 100 parts of N-vinyl-N-isopropylcarbamyl chloride and the whole heated for 6 hours at 75° C. A viscous solution is obtained having a dry content of 41.5% by weight. The polymer has a K valve of 52 (1% in toluene) and contains about 40% by weight of polymerized units of N-vinyl-isopropylcarbamyl chloride. The K value is a measure of the molecular weight of the polymer and is determined by the method described in Cellulosechemie, 13, p. 88 et seq. (1952). The end product gives clear coatings or films on wood, stone or concrete.

EXAMPLE 7 (application)

100 parts of n-hexane and 1 part of lauroyl peroxide are added to 100 parts of N-vinyl-N-cyclohexylcarbamyl chloride and the whole heated for 5 hours at 90° C. A viscous solution is obtained having a dry content of 39% by weight. The polymer has a K value of 44 (1% in toluene) and is a crosslinking agent for polyamines for the production of antistatic finishes on textiles and paper.

EXAMPLE 8 (application)

In a manner analogous to that described in Example 6, polymerization is carried out with vinyl-n-butylcarbamyl chloride having a boiling point of 75° C at 2 mm (prepared from 99 parts of acetaldehyde-n-butylimine analogously to Example 1) instead of with N-vinyl-N-isopropylcarbamyl chloride. A solution is obtained having a dry content of 48% by weight. The polymer has a K value of 57 (1% in toluene) and contains about 49% by weight of units of N-vinyl-N-n-butylcarbamyl chloride. The end product gives clear coatings of films on wood, stone and concrete.

EXAMPLE 9

N-vinyl-N-isopropylcarbamyl chloride:

85 parts of acetaldehydeisopropylimine is dissolved in 400 parts of benzene and this solution is added in portions with vigorous stirring and at a temperature of 5° C to a solution of 120 parts of phosgene in 300 parts of benzene. The reaction mixture is freed from unreacted phosgene by means of a stream of nitrogen. The remaining solution is divided into two equal portions.

One half of this solution is added in portions over a period of 30 minutes and while stirring to a boiling solution of 120 parts of triethylamine in 100 parts of benzene. One hour later the deposited crystals of triethylamine hydrochloride are suction filtered. The filtrate is subjected to fractional distillation. 52 parts (70% of the theory) of N-vinyl-N-isopropylcarbamyl chloride having a boiling point of 65° C at 2 mm is obtained.

The second portion of the solution is added in portions while stirring to a suspension of 140 parts of potassium carbonate in 100 parts of boiling benzene. After 3 hours, the mixture is suction filtered and distilled. 57 parts (77% of the theory) of N-vinyl-N-isopropylcarbamyl chloride is obtained.

EXAMPLE 10

N-1-cyclohexenyl-N-m-trifluoromethylphenylcarbamyl chloride:

A mixture of 120.5 parts of cyclohexanone-m-trifluoromethyl-phenylimine and 60 parts of thriethylamine is added in portions over a period of 30 minutes while stirring and at 10° to 20° C to a solution of 60 parts of phosgene in 200 parts of dry dioxane. The mixture is stirred for another hour and the end product is isolated in a manner analogous to that in Example 1. 129 parts of N-1-cyclohexenyl-N-m-trifluoromethylphenylcarbamyl chloride is obtained. It has a boiling point of 125° C at 0.5 mm and a melting point of 42° C after having been recrystallized from petroleum ether.

EXAMPLE 11

N-1-cyclohexenyl-N-o-methylphenylcarbamyl chloride:

187 parts of cyclohexanone-o-methylphenylimine and 120 parts of triethylamine are added in portions and at 0° to 10° C to a solution of 120 parts of phosgene in 400 parts of diethyl ether over a period of 1 hour in a manner analogous to that employed in Example 10. The mixture is stirred fo another hour. The end product is then isolated analogously to Example 10. 216 parts (87% of the theory) of N-1-cyclohexenyl-N-o-methylphenylcarbamyl chloride is obtained having a boiling point of 132° C at 0.3 mm.

EXAMPL 12

N-vinyl-N-methylcarbamyl chloride:

57 parts of acetaldeydemethylimine dissolved in 300 parts of toluene is added in portions over a period of 2 hours with vigorous stirring and at 0° C to a solution of 120 parts of phosgene in 200 parts of toluene. Unreacted phosgene is expelled by means of a stream of nitrogen. The reaction mixture is then introduced into a boiling solution of 120 parts of triethylamine in 100 parts of toluene. Three hours later the deposited triethylamine hydrochloride is filtered off and the filtrate is distilled 87 parts (81% of the theory) of N-vinyl-N-methylcarbamyl chloride having a boiling point of 52° C at 13 mm is obtained

EXAMPLE 13

N-vinyl-N-tert-butylcarbamyl chloride:

A solution of 99 parts of acetaldehyde-tert-butylimine and 101 parts of tert-butylamine in 350 parts of hexane is reacted with 120 parts of phosgene in 150 parts of hexane at −10° to 5° C. When the excess phosgene has been expelled with nitrogen, the triethylammonium chloride formed is filtered off. The filter residue is washed with a little hexane and the combined hexane solutions are evaported. The residue is distilled in vacuo.

152 parts of N-vinyl-N-tert-butylcarbamyl chloride with a boiling point of 85° C at 14 mm is obtained (82% of the theory).

EXAMPLES 14 to 19

In each case 90 parts of n-butyl acrylate in 100 parts of dioxane is reacted with 2 parts of azodiisobutyronitrile and 10 parts of n-vinylcarbamyl chloride (according to formula (I)) and polymerized for 5 hours at 80° C. The results are given in the following Table.

| No. | R¹ | R² | Yield of polymer in g | K value 1% in dimethyl-formamide | Proportion of comonomer in % determined via Cl proportion |
|---|---|---|---|---|---|
| 14 | cyclooctyl | H | 98 | 54 | 9.3 |
| 15 | cyclohexyl | H | 96 | 49 | 9.6 |
| 16 | isopropyl | H | 98.5 | 53 | 9.5 |
| 17 | n-butyl | H | 95 | 56 | 9.2 |
| 18 | n-hexyl | H | 98 | 54 | 9.5 |
| 19 | tetrahydro-dicyclo-pentadienyl | H | 94 | 42 | 9.1 |

We claim:

1. A process for the production of a compound of the formula

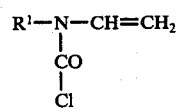

(I), wherein R¹ is tert-butyl or tert-pentyl, which process comprises reacting phosgene at a temperature of −30° to +150° C. with a Schiff base of the formula

(II), wherein R¹ has the same meaning given above, and in the presence of an additional base selected from the class consisting of tertiary amines and alkali metal carbonates.

2. A process as claimed in claim 1 wherein the reaction is carried out in a ratio of 1 to 1.2 moles of phosgene per mole of starting material (II).

3. A process as claimed in claim 1 wherein the reaction is carried out in the presence of a tertiary amine in an amount of 1 to 1.5 moles per mole of starting material (II).

4. A process as claimed in claim 1 carried out at a temperature of from 0° to 110° C.

5. A process as claimed in claim 1 carried out in the presence of an organic solvent which is inert under the reaction conditions.

6. A process as claimed in claim 1 in which R¹ is tert-butyl.

7. A process as claimed in claim 1 in which R¹ is tert-phenyl.

* * * * *